United States Patent [19]

Herrling

[11] 4,281,120

[45] Jul. 28, 1981

[54] 7H-1,3,4-THIADIAZOLO-[3,2-A]-PYRIMI-DIN-7-ONE-5-CARBOXYLIC COMPOUNDS

[76] Inventor: Siegfried Herrling, Dohlenweg 33, 5190 Stolberg, Fed. Rep. of Germany

[21] Appl. No.: 968,826

[22] Filed: Dec. 12, 1978

[51] Int. Cl.$^3$ .......................................... C07D 513/04
[52] U.S. Cl. ................................. 544/117; 544/58.6; 544/255; 260/243.3
[58] Field of Search ...................... 544/117, 58.6, 255; 424/248.51, 246, 251; 260/243.3

[56] References Cited
FOREIGN PATENT DOCUMENTS 2712932  10/1978  Fed. Rep. of Germany ........... 544/255

OTHER PUBLICATIONS

*Chemical Substance Index,* 1972–1976, 9th Collective, p. 8031cs.
Okahe et al., *Chem. Abstracts,* vol. 79, (1973), No. 32002z.

*Primary Examiner*—Henry R. Jiles
*Assistant Examiner*—R. W. Ramsuer

[57] ABSTRACT

Derivatives of 7H-1,3,4-thiadiazolo-[3,2-a]-pyrimidin-7-one-5-carboxylic acid having basic substituents in the 2-position, the alkyl esters and/or pharmaceutically useable salts of these compounds are new substances having immunstimulating properties, being especially valuable for antiinfectious therapy in mammals including man. The new products are prepared by reacting 2-amino-5-(basically substituted)-1,3,4-thiadiazoles with dialkylacetylenedicarboxylates and splitting the ester grouping in the obtained compound if desired and/or forming pharmaceutically acceptable salts.

8 Claims, No Drawings

7H-1,3,4-THIADIAZOLO-[3,2-a]-PYRIMIDIN-7-ONE-5-CARBOXYLIC COMPOUNDS

DESCRIPTION OF THE INVENTION

The present invention relates to new heterocyclic compounds of the general formula (I):

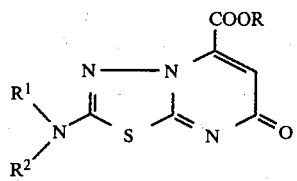

wherein R represents hydrogen or an alkyl radical with 1 to 5 carbon atoms, $R^1$ and $R^2$ which may be the same or different represent alkyl radicals with 1 to 5 carbon atoms or together with the nitrogen atom to which they are attached form a 5- to 7-membered heterocyclic ring which may be substituted by one or more alkyl groups, preferably 1 to 4 alkyl groups, containing 1 to 3 carbon atoms which may also be interrupted by an oxygen or a sulfur atom or a group $R^3$-N<, wherein $R^3$ represents an alkyl radical with 1 to 4 carbon atoms, a monocyclic aryl radical or an aralkyl radical with 1 or 2 carbon atoms in the alkylene group and pharmaceutically acceptable salts of these compounds.

Other objects of the present invention are medicaments containing compounds of formula (I) and a process for the preparation of the new compounds.

The compounds of formula (I) and the salts thereof show pronounced activity in stimulating the immune system such as in mammals and, by virtue of this property, are valuable therapeutic agents for diseases where an increase in the body's defense is required, expecially when the immunity of the diseased organism is disturbed or inadequately developed. The compounds of the invention are especially valuable for antiinfectious therapy in mammals. Examples of such diseases which can be treated with the medicaments according to the invention are virus infections, and bacterial infections.

In the case when R represents hydrogen the pharmaceutically useable salts of the compounds of formula (I) preferably are derived from suitable bases. Such salts are preferably the sodium, potassium or ammonium salts. There may be used, however, also the calcium, magnesium, lithium, aluminium and amine salts, such amines being for instance triethylamine, N-ethylpiperidine, morpholine, ethanolamines or benzylamine.

The compounds of formula (I) are also capable of forming salts with acids such as hydrochloric acid, hydrobromic acid, sulfuric acid, phosphoric acid, methane-, benzene- or toluene-sulfonic acid, formic acid, acetic or propionic acid, maleic acid, tartaric acid, benzoic acid, salicylic acid, nicotinic acid and others.

If the group

represents a heterocyclic radical it may be derived from heterocycles like pyrrolidine, 2,5-dimethylpyrrolidine, piperidine, 2-, 3- or 4-methylpiperidine, 2,6-dimethyl piperidine, 2,6-diethylpiperidine, 2,4,6-trimethylpiperidine, morpholine, thiomorpholine, $N^4$-methyl-, $N^4$-ethyl- or $N^4$-propyl-piperazine, $N^4$-benzylpiperazine, hexamethylene-imine and similar heterocycles.

If, however, $R^1$ and $R^2$ represent lower alkyl radicals they preferably are propyl or butyl radicals.

In order to demonstrate the effects of compounds of formula (I) against virus infections, mice were infected with hepatitis viruses (murine). 24, 48, 72 and 96 hours later, respectively, they were treated orally each time with 0.1 mg of ethyl 2-pyrrolidino-7H-1,3,4-thiadiazolo-[3,2-a]-pyrimidin-7-one-5-carboxylate per kg body weight whereupon 80% of the animals survived. On treatment of infected animals only once (24 hours after the infection) with an oral dose of 1 mg of ethyl 2-morpholino-7-H-1,3,4-thiadiazolo-[3,2-a]-pyrimidin-7-one-5-carboxylate per kg body weight 50% of the animals survived. From untreated, infected control animals 90% died due to the infection.

These tests results demonstrate the surprising therapeutic value of the compounds of formula (I) especially for the treatment of virus infections in mammals.

Another object of the invention are medicaments, for human or veterinary therapy which contain one or more active ingredients of the general formula (I) in such a quantity that the daily dose for human therapy amounts up to about 2,500 mg and preferably 5 to 500 mg. These amounts may be increased or decreased depending upon the degree of illness and the general condition of the patient. The treatment is best carried out with 2 to 3 single doses per day. Suitable formulations for oral administration are standard tablets, dragees, syrups, drops and other pharmaceutical formulations commonly used for oral therapy including for example those from which the active ingredients have a delayed release.

The medicaments of the invention may also be applied rectally in the form of suppositories prepared in the usual manner.

Since the active ingredients of general formula (I), particularly when they are in the form of pharmaceutically useable salts, are readily soluble in water and are stable substances under normal conditions, the medicaments according to the invention also include sterile, injectable solutions of these active principles.

Other formulations according to the invention include sprays (containing or free of propellants) especially for intranasal application and for inhalation.

The present invention also relates to the preparation of the compounds of the general formula (I) and their pharmaceutically useable salts. The new substances are prepared by reacting a 2-amino-1,3,4-thiadiazole of the following formula (II):

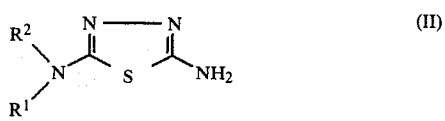

wherein $R^1$ and $R^2$ have the same meaning as above with a dialkyl acetylenedicarboxylate of the formula $R^4OOC-C\equiv C-COOR^4$, in which $R^4$ represents an alkyl radical of 1 to 5 carbon atoms.

If in a compound of the general formula (I) R represents an alkyl radical from 1 to 5 carbon atoms it is readily possible, if desired, to saponify the ester group —COOR then present and optionally to convert the resulting compound of formula (I) containing a free carboxylic group into pharmaceutically acceptable salts by reaction with suitable bases, examples of which are mentioned herein above.

Pharmaceutically acceptable salts of the compounds of general formula (I) with acids preferably are prepared by reacting equimolar amounts of a compound of formula (I) and of the selected acid in the presence of a solvent, especially a polar solvent, and thereafter isolating the salt by eliminating the solvent (for example by freeze drying) or by adding a diluent which is miscible with the solvent and in which the desired salt is insoluble or sparingly soluble whereupon the salt precipitates and may be filtered off.

The compounds of formula (II) have not been described in the literature before the present invention was made. These compounds and their preparation accordingly form another object of the invention.

The compounds of the general formula (II) are prepared by reacting a 1,3,4-thiadiazole of the following formula (III):

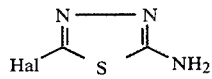

(III)

wherein Hal is a halogen atom, preferably a chlorine or a bromine atom with an amine of the following formula (IV):

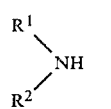

(IV)

wherein $R^1$ and $R^2$ have the same meaning as above.

This reaction conveniently proceeds by heating the reactants in the presence of a solvent, preferably an alcoholic solvent, and in the presence of a compound capable of binding the hydrogen halide which is formed during the reaction. Such hydrogen halide binding compound preferably is an excess of the amine of the general formula (IV).

The reaction of the compound of the general formula (II) with the dialkyl acetylenedicarboxylate is carried out in the presence of a solvent or suspending agent, optionally at an elevated temperature. Suitable solvents or suspending agents are, for example, lower aliphatic alcohols, especially methanol, ethanol and propanol, ethyl or propyl acetate, acetonitrile, tetrahydrofuran, dioxane, chlorobenzene, glacial acetic acid or dimethylformamide. It is also possible initially to react the reactants in a solvent, ethanol for example, and then to complete the ring-closing reaction by heating in another solvent having a higher boiling point than the first one used, for example chlorobenzene.

The formation of resin-like, dark colored by-products can be largely avoided by working in the absence of light and air.

The following Examples serve to illustrate the production of the compounds of formulae (I) and (II).

No importance was attached to obtaining optimum yields. All the temperatures quoted are uncorrected.

EXAMPLE 1

A mixture of 9 g of 2-amino-5-bromo-1,3,4-thiadiazole (0.05 mole), 9.1 g of morpholine (0.105 mole) and 150 ml ethanol was refluxed for 6 hours. After standing overnight at room temperature the precipitate was filtered off, suspended in water, again filtered off and then dried. Thus 2-amino-5-morpholino-1,3,4-thiadiazole is obtained in a yield of 43.6% of the theoretical yield. Melting point: 186°–188° C.

| $C_6H_{10}N_4OS$ (186.25) | C | H | N | S |
|---|---|---|---|---|
| calculated | 38.69% | 5.41% | 30.08% | 17.22% |
| found: | 38.68% | 5.33% | 29.52% | 17.41% |

By using n-propanol as the solvent instead of ethanol the same product is obtained in a yield of 65.1% of the theoretical yield.

EXAMPLE 2

A mixture of 16 g of 2-amino-5-bromo-1,3,4-thiadiazole, 13.3 g of pyrrolidine and 250 ml of n-propanol was boiled under reflux for 6 hours, stored overnight at room temperature and thereafter filtered. The residue was suspended in water and treated with dilute sodium hydroxide solution until alkaline. The product was filtered off, washed with water and dried. The thus obtained 2-amino-5-pyrrolidino-1,3,4-thiadiazole may be recrystallized from water.

Yield: 13.7 g=90.5% of the theoretical yield.

Melting point: 231°–234° C. with decomposition.

From the alkaline aqueous filtrate the excess of pyrrolidine may be recovered in a manner known per se.

EXAMPLE 3

Following the procedure described in Example 2 but using the respective amines in place of the pyrrolidine used in Example 2 the following compounds of the general formula (II) were obtained.

| $\begin{array}{c} R^1 \\ \diagdown \\ \phantom{R}N- \\ \diagup \\ R^2 \end{array}$ | melting point °C. | yield (% of the theoretical) |
|---|---|---|
| (a) 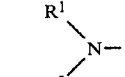 | 205–207 | 81.1 |
| (b) 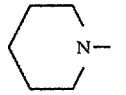 | 147–149 | 90.9 |
| (c) 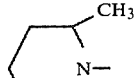 | 168–170 | 93.5 |
| (d) 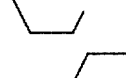 | 193–195 | 70.7 |
| (e) 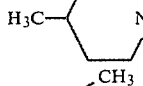 | 172–174 | 62.7 |

-continued

| $\begin{array}{c}R^1\\ \diagdown\\ N-\\ \diagup\\ R^2\end{array}$ | melting point °C. | yield (% of the theoretical) |
|---|---|---|
| (f) phenyl-piperazinyl | 226–228 | 87.0 |
| (g) benzyl-piperazinyl | 187–189 | 98.3 |
| (h) phenethyl-piperazinyl | 168–170 | 96.8 |
| (i) heptamethyleneimino | 177–179 | 69.2 |
| (k) $(n\text{-}C_3H_7)_2\text{—N—}$ | 138–140 | 87.5 |
| (l) $(n\text{-}C_4H_9)_2\text{—N—}$ | 105–107 | 93.1 |

EXAMPLE 4

3.5 g of the 2-amino-5-morpholino-1,3,4-thiadiazole obtained in Example 1 were mixed with 40 ml of absolute ethanol and then 3.2 g of diethyl acetylendicarboxylate was added. The reaction mixture was heated on a water bath to about 60° C. until a clear solution was formed. This was stored overnight at room temperature and then evaporated in vacuo to dryness. The residue was triturated with a small amount of cold ethanol, filtered off, washed with ether and finally dried. Thus 3.8 g, corresponding to 65.2% of the theoretical yield, of ethyl 2-morpholino-7H-1,3,4-thiadiazolo-[3,2-a]-pyrimidin-7-one-5-carboxylate, melting at 151° to 153° C., was obtained.

| $C_{12}H_{14}N_4O_4S$ (310.34) | C | H | N | S |
|---|---|---|---|---|
| Calculated: | 46.44% | 4.55% | 18.05% | 10.33% |
| Found: | 46.46% | 4.46% | 18.12% | 10.33% |

EXAMPLE 5

8.5 g of 2-amino-5-pyrrolidino-1,3,4-thiadiazole were added to 300 ml of ethanol and mixed with 8.5 g of diethyl acetylenedicarboxylate. On heating for 10 to 20 minutes to about 50° to 60° C. a clear solution was obtained which after standing overnight at room temperature was evaporated in vacuo to dryness. The residue was triturated with a small amount of cold ethyl acetate, filtered off, washed with ether and then dried. 8.4 g (57.1% of the theoretical yield) of ethyl 2-pyrrolidino-7H-1,3,4-thiadiazolo-[3,2-a]pyrimidin-7-one-5-carboxylate were thus obtained.
Melting point: 138°–140° C.

| $C_{12}H_{14}N_4O_3S$ (294.34) | C | H | N |
|---|---|---|---|
| Calculated: | 48.96% | 4.97% | 19.04% |
| Found: | 48.34% | 4.72% | 19.18% |

EXAMPLE 6

The procedure used was as described in Example 5. However, there were used 9.2 g of 2-amino-5-piperidino-1,3,4-thiadiazole, 8.5 g of diethyl acetylenedicarboxylate and 200 ml of ethanol. Thus 9.8 g (63.7% of the theoretical yield) of ethyl 2-piperidino-7H-1,3,4-thiadiazolo-[3,2-a]-pyrimidin-7-one-5-carboxylate, melting at 125° to 127° C., were obtained.

| $C_{13}H_{16}N_4O_3S$ (308.36) | C | H | N | S |
|---|---|---|---|---|
| Calculated: | 50.64% | 5.23% | 18.17% | 10.40% |
| Found: | 50.26% | 5.07% | 18.32% | 10.77% |

In an analogous manner the compounds of formula (I) (R=ethyl) listed in the following table were obtained:

| $\begin{array}{c}R^1\\ \diagdown\\ N-\\ \diagup\\ R^2\end{array}$ | Yield (% of the theoretical) | melting point °C. | C% Calc. | C% Found | H% Calc. | H% Found | N% Calc. | N% Found | S% Calc. | S% Found |
|---|---|---|---|---|---|---|---|---|---|---|
| 2-methylpiperidino | 49.8 | 87–89 | 52.20 | 51.96 | 5.63 | 5.71 | 17.39 | 16.86 | 9.94 | 9.94 |
| 4-methylpiperidino | 54.6 | 127–129 | 52.20 | 52.19 | 5.63 | 5.59 | 17.39 | 16.88 | 9.94 | 10.21 |
| 2,6-dimethylpiperidino | 80.0 | 99–103 (with decomposition) | 53.50 | 53.07 | 5.98 | 5.92 | 16.67 | 16.17 | 9.53 | 9.57 |
| 4-methylpiperazino | 54.1 | 151–153 | 48.28 | 47.75 | 5.30 | 5.18 | 21.66 | 21.77 | 9.90 | 9.93 |

| $R^1$<br>$\phantom{R^1}\diagdown$<br>$\phantom{R^1\diagdown}N-$<br>$\phantom{R^1}\diagup$<br>$R^2$ | Yield (% of the theoretical) | melting point °C. | C% Calc. | Found | H% Calc. | Found | N% Calc. | Found | S% Calc. | Found |
|---|---|---|---|---|---|---|---|---|---|---|
|  | 49.8 | 155–157 | 56.09 | 56.14 | 4.97 | 4.94 | 18.17 | 17.86 | 8.32 | 8.29 |
| 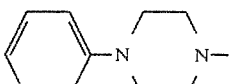 | 52.3 | 143–145 | 57.13 | 56.91 | 5.29 | 5.14 | 17.53 | 17.21 | 8.03 | 8.06 |
| 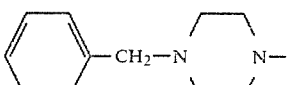 | 47.4 | 154–156 | 58.10 | 58.19 | 5.60 | 5.50 | 16.95 | 17.03 | 7.74 | 7.79 |

EXAMPLE 7

Following the procedure described in Example 5 but using dimethyl, di-n-propyl or di-n-butyl acetylenedicarboxylate in place of the diethyl ester used in Example 5 there were obtained the following esters of 2-pyrrolidino-7H-1,3,4-thiadiazolo-[3,2-a]-pyrimidin-7-one-5-carboxylic acid:

|  | Melting point | Yield |
|---|---|---|
| methyl ester | 150–152° C. | 43.1% |
| n-propyl ester | 104–106° C. | 45.6% |
| n-butyl ester | 111–113° C. | 39.8% |

EXAMPLE 8

A mixture of 7.3 g 2-amino-5-hexamethyleneimino-1,3,4-thiadiazole, 6.3 g of diethyl acetylenedicarboxylate and 200 ml of ethanol was used in the procedure described in Example 5. Thus 7 g (61.5% of the theoretical yield) of ethyl 2-hexamethyleneimino-7H-1,3,4-thiadiazolo-[3,2-a]-pyrimidin-7-one-5-carboxylate were obtained.

Melting point: 135°–137° C.

| $C_{14}H_{18}N_4O_3S$ (322.4) | C | H | N | S |
|---|---|---|---|---|
| Calculated: | 52.16% | 5.63% | 17.38% | 9.94% |
| Found: | 52.19% | 5.51% | 17.26% | 9.90% |

EXAMPLE 9

The procedure used was as in Example 5. However, there were reacted 10 g of 2-amino-5-[di-(n-propyl)amino]-1,3,4-thiadiazole and 8.5 g of diethyl acetylenedicarboxylate in the presence of 200 ml of ethanol to give 10.2 g (63% of the theoretical yield) of ethyl 2-[di-(n-propyl)amino]-7H-1,3,4-thiadiazolo-[3,2-a]-pyrimidin-7-one-5-carboxylate, melting at 95°–97° C.

| $C_{14}H_{20}N_4O_3S$ (324.4) | C | H | N | S |
|---|---|---|---|---|
| Calculated: | 51.83% | 6.21% | 17.27% | 9.88% |
| Found: | 51.83% | 6.13% | 17.11% | 9.91% |

In the same manner ethyl 2-[di-(n-butyl)-amino]-7H-1,3,4-thiadiazolo[3,2-a]-pyrimidin-7-one-5-carboxylate melting at 71°–72° C. was obtained in a yield of 57.1% of the theoretical yield when using 2-amino-5-[di-(n-butyl)amino]-1,3,4-thiadiazole.

EXAMPLE 10

Following the procedure described in Example 5, 4.9 g of 2-amino-5-[di-(isopropyl)-amino]-1,3,4-thiadiazole were reacted with 4.2 g of diethyl acetylenedicarboxylate in the presence of 100 ml of ethanol. The ethyl 2-[di-(isopropyl)-amino]-7H-1,3,4-thiadiazolo-[3,2-a]-pyrimidin 7-one-5-carboxylate obtained was recrystallized from ethyl acetate.

Melting point: 81°–82° C.

Yield: 4.3 g = 54.4% of the theoretical yield.

| $C_{14}H_{20}N_4O_3S$ (324.4) | C | H | N | S |
|---|---|---|---|---|
| Calculated: | 51.83% | 6.21% | 17.27% | 9.88% |
| Found: | 51.75% | 6.08% | 16.89% | 9.83% |

EXAMPLE 11

5.9 g of ethyl 2-pyrrolidino-7H-1,3,4-thiadiazolo-[3,2-a]-pyrimidin-7-one-5-carboxylate (obtained according to Example 5) were introduced, while stirring, into 50 ml of a 2 normal sodium hydroxide solution which had been warmed to 50°–55° C. Stirring at this temperature was continued until a clear solution had been formed, whereupon the mixture was chilled, stirred and acidified with 2 normal hydrochloric acid. The precipitate was filtered off, washed with water and dried. The 2-pyrrolidino-7H-1,3,4-thiadiazolo-[3,2-a]-pyrimidin-7-one-5-carboxylic acid thus obtained melts at 265° C. with decomposition. It is readily soluble in aqueous alkalis and also in solutions of ammonia or amines, respectively. From such solutions provided stoichiometric amounts of the reactants were used, the salts may be isolated, expecially by lyophilisation. They form solids which are easily soluble in water.

Following the processes described above, particularly as performed in any of the Examples it is also possible to obtain inter alia the following compounds of general formula (I) and to prepare and use the respective derivatives of 2-amino-1,3,4-thiadiazole of the general formula (II) as intermediates:

ethyl 2-thiomorpholino-7H-1,3,4-thiadiazolo-[3,2-a]-pyrimidin-7-one-5-carboxylate and the corresponding free carboxylic acid;

methyl 2-(N⁴-ethylpiperazino)-7H-1,3,4-thiadiazolo-[3,2-a]-pyrimidin-7-one-5-carboxylate;

ethyl 2-diethylamino-7H-1,3,4-thiadiazolo-[3,2-a]-pyrimidin-7-one-5-carboxylate;

butyl 2-dimethylamino-7H-1,3,4-thiadiazolo-[3,2-a]-pyrimidin-7-one-5-carboxylate;

2-(2',5'-dimethylpyrrolidino)-7H-1,3,4-thiadiazolo-[3,2-a]-pyrimidin-7-one-5-carboxylic acid;

ethyl 2-(2',4'-dimethyl- or -diethyl-piperidino)-7H-1,3,4-thiadiazolo-[3,2-a]-pyrimidin-7-one-5-carboxylate;

methyl 2-[di-(isopropyl)-amino]-7H-1,3,4-thiadiazolo-[3,2-a]-pyrimidin-7-one-5-carboxylate;

2-(4'-isopropylpiperidino)-7H-1,3,4-thiadiazolo-[3,2-a]-pyrimidin-7-one-5-carboxylic acid;

ethyl 2-(2'-methyl- or -ethyl-pyrrolidino)-7H-1,3,4-thiadiazolo-[3,2-a]-pyrimidin-7-one-5-carboxylate;

methyl 2-(2',2',5',5'-tetramethylpyrrolidino)-7H-1,3,4-thiadiazolo-[3,2-a]-pyrimidin-7-one-5-carboxylate;

ethyl 2-(2',4',6'-trimethylpiperidino)-7H-1,3,4-thiadiazolo-[3,2-a]-pyrimidin-7-one-5-carboxylate;

methyl 2-(3'-methylpyrrolidino)-7H-1,3,4-thiadiazolo-[3,2-a]-pyrimidin-7-one-5-carboxylate;

butyl 2-(2'-n-butylpyrrolidino)-7H-1,3,4-thiadiazolo-[3,2-a]-pyrimidin-7-one-5-carboxylate;

ethyl 2-(N⁴-n-butylpiperazino)-7H-1,3,4-thiadiazolo-[3,2-a]-pyrimidin-7-one-5-carboxylate and, from these esters, the corresponding acids and/or salts thereof.

What is claimed is:

1. Heterocyclic compounds of the following general formula (I)

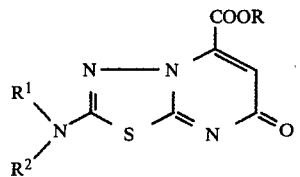
(I)

wherein R represents hydrogen or an alkyl radical with 1 to 5 carbon atoms, $R^1$ and $R^2$, which may be the same or different, represent alkyl radicals with 1 to 5 carbon atoms or together with the nitrogen atom to which they are attached form a 5- to 7-membered heterocyclic ring which may be substituted by one or more alkyl groups containing 1 to 3 carbon atoms which may also be interrupted by an oxygen or a sulfur atom or a $R^3$-N< group, wherein $R^3$ represents an alkyl radical with 1 to 4 carbon atoms, a monocyclic aryl radical or an aralkyl radical with 1 or 2 carbon atoms in the alkylene group and the pharmaceutically acceptable salts thereof.

2. The heterocyclic compounds of claim 1, wherein said compounds are of the following general formula:

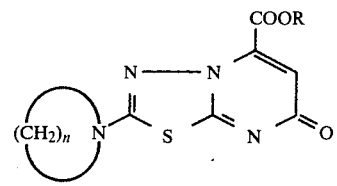

wherein R is as defined in claim 1 and n is 4,5 or 6 and the pharmaceutically acceptable salts thereof.

3. The heterocyclic compounds of claim 1, wherein said compounds are of the following general formula:

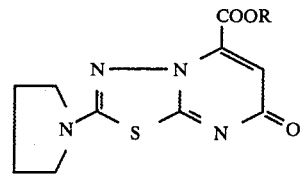

wherein R is as defined in claim 1, and the pharmaceutically acceptable salts thereof.

4. The heterocyclic compounds of claim 1, wherein said compound is ethyl 2-pyrrolidino-7H-1,3,4-thiadiazolo-[3,2-a]-pyrimidin-7-one-5-carboxylate and the pharmaceutically acceptable salts thereof with an acid.

5. The heterocyclic compounds of claim 1, wherein said compounds are of the following general formula:

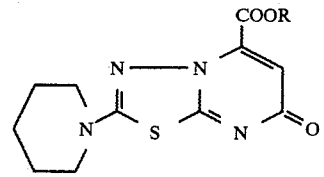

wherein R is as defined in claim 1 and the pharmaceutically acceptable salts thereof.

6. The heterocyclic compounds of claim 1, wherein said compound is ethyl 2-piperidino-7H-1,3,4-thiadiazolo-[3,2-a]-pyrimidin-7-one-5-carboxylate and the pharmaceutically acceptable salts thereof with an acid.

7. The heterocyclic compounds of claim 1, wherein said compounds are of the following general formula

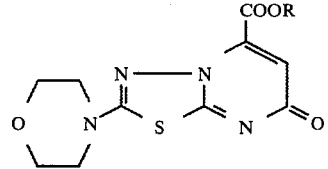

wherein R is as defined in claim 1, and the pharmaceutically acceptable salts thereof.

8. The heterocyclic compounds of claim 1 wherein said compound is ethyl 2-morpholino-7H-1,3,4-thiadiazolo-[3,2-a]-pyrimidin-7-one-5-carboxylate and the pharmaceutically acceptable salts thereof with an acid.

* * * * *